Figure 1:
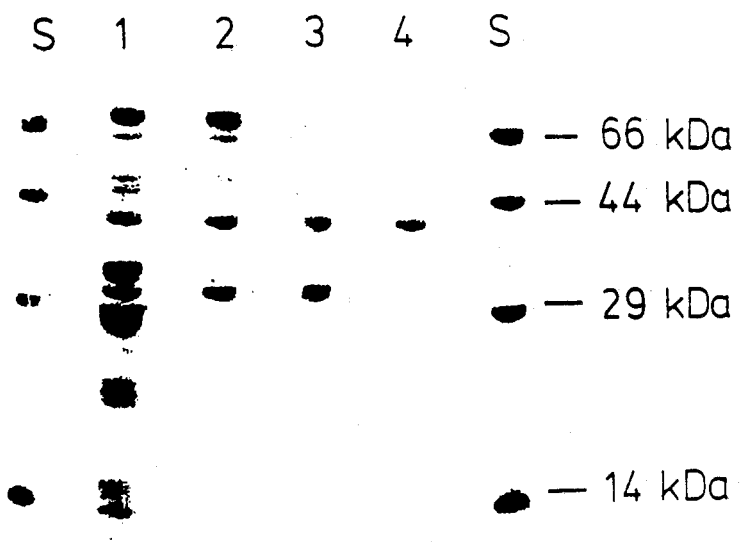

United States Patent [19]

Gatz et al.

[11] Patent Number: 4,963,488

[45] Date of Patent: Oct. 16, 1990

[54] DNA SEQUENCES, RECOMBINANT DNA MOLECULES AND PROCESS FOR THE PREPARATION OF THE ENZYME MUTAROTASE FROM ACINETOBACTER CALCOACETICUS

[75] Inventors: Christiane Gatz, Marl; Joachim Altschmied, Munich; Hans G. Gassen, Darmstadt; Wolfgang Hillen, Erlangen, all of Fed. Rep. of Germany

[73] Assignee: Merck Patent Gesellschaft mit beschrankter Haftung, Darmstadt, Fed. Rep. of Germany

[21] Appl. No.: 406,888

[22] Filed: Sep. 13, 1989

Related U.S. Application Data

[63] Continuation of Ser. No. 903,319, Sep. 3, 1986, abandoned.

[30] Foreign Application Priority Data

Sep. 3, 1985 [DE] Fed. Rep. of Germany ....... 3531360

[51] Int. Cl.$^5$ .......................... C12N 9/90; C12N 2/21; C12N 15/52; C12N 15/70

[52] U.S. Cl. .................................. 435/233; 435/69.1; 435/71.1; 435/172.1; 435/172.3; 435/252.3; 435/252.33; 435/320; 435/849; 536/27; 935/6; 935/9; 935/14; 935/22; 935/38; 935/60; 935/72; 935/73

[58] Field of Search ................... 435/183, 69.1, 71.1, 435/172.1, 172.3, 233, 252.31, 252.33, 320, 849; 536/27; 935/6, 9, 14, 22, 38, 60, 72, 73

[56] References Cited

PUBLICATIONS

Mulhern et al., J. Biol. Chem (1973), (12), pp. 4163-4173.
Bently et al., J. Biol. Chem (1960), 235 1219-1223.
Bailey et al., J. Biol. Chem (1969 (244), pp. 781-788.
Wallenfels et al., Methods in Enzymology, (1966), vol. IX, pp. 608-610.
Thomspon, Genetic Engineering 3 (1982), pp. 2, 23-28.

Primary Examiner—Richard A. Schwartz
Assistant Examiner—Richard C. Peet
Attorney, Agent, or Firm—Millen, White & Zelano

[57] ABSTRACT

The invention relates to DNA sequences, recombinant DNA molecules and transformed host organisms, and to their use in a process for the genetic engineering preparation of a polypeptide having the biological activity of the enzyme mutarotase.

17 Claims, 10 Drawing Sheets

```
                    ATLNVKPYGTTQNGQKVDLYTMSNNNG......................    50
    N-Terminus      ***********************
    CB 1            ********************
                                CB 2  *****

..................................................   100

............................................   150

..............TDQPTVVNLTNHSYFNLSGAGNNP...      200
                              F 42    ***********************

............................MPKAI........      250
                                              CB 3   ****

.............................TMQVLTTEPSVQMYTA  300
                                                CB 5       ***
                                         F 38   ****************
                                                ARG 1       ***

DHLLGNIVGANGVLYRQADALALETQHFPDSPNQPTFPSTRLNPNQTYNS              350
    CB 5    *********************************************
    F 38    ***********
    ARG 1   *************                      ARG 3  *********
                    ARG 2    ************************
                    VTVFKFGVQK
    ARG 3           **********
```

FIG. 4 pWH 1318 (~9700 bp)

pWH 1319 (5860 bp)

FIG. 10

```
ATGAAAAAATTAGCAATTTTAGGTGTTACGGTTTATAGCTTTGCACAACT
GGCAAATGCAGCAACGTTAAATGTAAAATCATATGGTACGACTCAAAATG
GCCAAAAAGTTGATCTATACACCATGAGTAATAACAATGGAGTCTCGGTA
TCTTTTATTAGTTTTGGTGGTGTAATTACACAAATCTTGACTCCCGATGC
CCAAGGCAAACAAAATAATATCGTTTTGGGCTTTGATGACTTAAAAGGCT
ATGAAGTCACTGATACCAAGGAAGGTATTCATTTTGGCGGATTAATTGGT
CGTTATGCGAACCGGATTGGCAATGCTAAATTTAGCTTAGATGGAAAAAC
GTATAACCTCGAAAAAAATAATGGTCCGAACTCATTACATAGCGGCAATC
CTGGTTTTGATAAACGTGTTTGGCAAGTTAAGCCCCTCGTTTCTAAAGGT
GAAACCGTTAAAGCTTCTCTTAAGTTAACCAGCCCAAATGGAGATCAAGG
TTTTCCCGGAAAATTAGATGTAGAAGTGATCTACAGTCTTTCAGATCAAA
ATGAATTCAAGATTGAATATAAAGCCAAAACTGATCAGCCTACAGTCGTC
AACCTTACCAACCACAGTTATTTCAACTTATCAGGTGCTGGGAACAATCC
TTATGGCGTGCTAGATCATGTGGTACAACTCAATGCAGGCCGTATTCTGG
TAACCGATCAAAACTCTTTACCAACAGGTGAAATTGCTTCAGTTGCAGGT
ACGCCTTTTGATTTTCGGATGCCTAAAGCAATCGTAAAGATATTCGAGC
AAATAATCAGCAATTGGCCTATGGATATGGCTATGACCAAACTTGGGTAA
TTAATCAAAAGTCTCAAGGAAAACTCAATCTTGCAGCTATTGTGGTTGAT
CCAAAATCTAAACGGACCATGCAAGTCTTAACCACTGAACCAAGCGTCCA
AATGTATACAGCCGATCATTTATTAGGAAATATTGTTGGCGCAAATGGCG
TACTCTATCGACAAGCAGACGCACTAGCATTAGAAACACAGCATTTTCCA
GACAGCCCGAATCAACCAACTTTCCCGTCTACACGTTTAAACCCAAATCA
AACTTATAACAGTGTTACCGTATTTAAGTTTGGTGTTCAAAAA
```

FIG. 11

```
AlaThrLeuAsnValLysSerTyrGlyThrThrGlnAsnGlyGlnLysVal
AspLeuTyrThrMetSerAsnAsnAsnGlyValSerValSerPheIleSer
PheGlyGlyValIleThrGlnIleLeuThrProAspAlaGlnGlyLysGln
AsnAsnIleValLeuGlyPheAspAspLeuLysGlyTyrGluValThrAsp
ThrLysGluGlyIleHisPheGlyGlyLeuIleGlyArgTyrAlaAsnArg
IleGlyAsnAlaLysPheSerLeuAspGlyLysThrTyrAsnLeuGluLys
AsnAsnGlyProAsnSerLeuHisSerGlyAsnProGlyPheAspLysArg
ValTrpGlnValLysProLeuValSerLysGlyGluThrValLysAlaSer
LeuLysLeuThrSerProAsnGlyAspGlnGlyPheProGlyLysLeuAsp
ValGluValIleTyrSerLeuSerAspGlnAsnGluPheLysIleGluTyr
LysAlaLysThrAspGlnProThrValValAsnLeuThrAsnHisSerTyr
PheAsnLeuSerGlyAlaGlyAsnAsnProTyrGlyValLeuAspHisVal
ValGlnLeuAsnAlaGlyArgIleLeuValThrAspGlnAsnSerLeuPro
ThrGlyGluIleAlaSerValAlaGlyThrProPheAspPheArgMetPro
LysAlaIleValLysAspIleArgAlaAsnAsnGlnGlnLeuAlaTyrGly
TyrGlyTyrAspGlnThrTrpValIleAsnGlnLysSerGlnGlyLysLeu
AsnLeuAlaAlaIleValValAspProLysSerLysArgThrMetGlnVal
LeuThrThrGluProSerValGlnMetTyrThrAlaAspHisLeuLeuGly
AsnIleValGlyAlaAsnGlyValLeuTyrArgGlnAlaAspAlaLeuAla
LeuGluThrGlnHisPheProAspSerProAsnGlnProThrPheProSer
ThrArgLeuAsnProAsnGlnThrTyrAsnSerValThrValPheLysPhe
GlyValGlnLys
```

DNA SEQUENCES, RECOMBINANT DNA MOLECULES AND PROCESS FOR THE PREPARATION OF THE ENZYME MUTAROTASE FROM ACINETOBACTER CALCOACETICUS

This application is a continuation of application Ser. No. 903,319, filed Sept. 3, 1986, now abandoned.

BACKGROUND OF THE INVENTION

This invention relates to the preparation of a DNA sequence which codes for a polypeptide having the biological activity of the enzyme mutarotase.

In addition, the invention relates to recombinant DNA molecules, that is to say cloning and expression vectors, for use in the preparation of a polypeptide having the biological activity of the enzyme mutarotase, and to host organisms transformed with such vectors, for example bacteria, yeasts, other fungi, and animal or human cells.

The invention also relates to the use of the said polypeptide having the biological activity of the enzyme mutarotase for increasing the rate of enzymatic detection reactions or conversions of aldoses.

Mutarotase (aldose 1-epimerase, EC 5.1.3.3) is known to increase the rate of setting up equilibrium between the α- and β-anomers of aldohexoses, for example, between α- and β-glucose or α- and β-galactose. The main use of the enzyme is in analytical biochemistry for increasing the rate of enzymatic detection reactions for aldoses by means of enzymes specific for the α- or β-form, in which the setting up of the equilibrium between the two anomers is the rate-determining step, for example in determination methods with glucose dehydrogenase, glucose oxidase or galactose dehydrogenase.

Industrial use would be of interest, for example for the glucoamylase/glucose isomerase process, because the enzyme glucoamylase liberates β-glucose which cannot be converted into the α-form by the glucose isomerase until mutarotation has taken place.

Mutarotase is widespread in nature, occurring in various microorganisms (bacteria, yeasts and filamentous fungi), in plants and in animal tissues.

The only considerable enzyme contents allowing isolation of mutarotase on the industrial scale have to date been found in the kidneys of mammals (cattle, pigs); all the known commercial products are prepared from kidneys. It is known, from Bailey, Meth. Enzymol. 1975, 478, that the content of mutarotase activity per g of fresh weight in bovine kidneys is more than 60 times that in, for example, Escherichia coli. A process for the microbiological preparation of mutarotase from strains of Aspergillus niger was described for the first time in Biochim. Biophys. Acta 662, 285 (1981). According to this, the mutarotase activity obtained from the best strain was 4.4 mU/ml of culture broth, the Michaelis constant being 50 mM and the pH optimum being in the range 5 to 7.

However, using the said microbiological process the enzyme mutarotase can only be obtained in lower yields than with the process for preparation from bovine kidneys. In addition, the properties of the enzyme from Aspergillus niger are unfavorable for setting up the equilibrium within the scope of enzymatic determinations of aldoses.

SUMMARY OF THE INVENTION

Thus, it is an object of this invention to make available a polypeptide having the biological activity of the enzyme mutarotase, and to provide a genetic engineering process which allows the industrial preparation of this protein in large amounts.

The term "polypeptide having the biological activity of the enzyme mutarotase" means a polypeptide or protein whose amino acid sequence corresponds to natural mutarotase, e.g., from Acinetobacter calcoaceticus, is similar to this amino acid sequence or comprises only a part thereof sufficient to provide the mentioned biological activity. According to the invention, corresponding fusion proteins are also termed "polypeptides having the biological activity of the enzyme mutarotase."

The species which form mutarotase and which are preferably used are microorganisms of the genus Acinetobacter. Of these, those of the strains Acinetobacter calcoaceticus DSM 30007, DSM 30008, DSM 30010 or DSM 30011, in particular DSM 30008, are preferred, as are their mutants or variants into which parts of the appropriate genetic information have been introduced.

Suitable host organisms into which the DNA coding for mutarotase can be transplanted are primarily microorganisms, but also plant, animal or human cells. Microorganisms, such as bacteria, yeasts and filamentous fungi, in particular E. coli bacteria, are preferred.

To make available a genetic engineering process for the preparation of a polypeptide having the biological activity of the enzyme mutarotase, according to the invention the following steps can be carried out:

First, the microorganism Acinetobacter calcoaceticus strain No. DSM 30008, for example, is cultivated in a suitable culture medium. Then the natural mutarotase of the microorganism is isolated from this culture and subjected to biochemical protein analysis. After the amino acid part-sequences of the said mutarotase have been established, the oligonucleotides corresponding to amino acid positions 12 to 17 and 353 to 359 of the mutarotase polypeptide are synthesized. Since the genetic code is degenerate, there are various possibilities for the sequences of the oligodeoxynucleotides corresponding to each of these amino acid positions. Hence, according to the invention several different oligodeoxynucleotides are synthesized for each, and are used as oligonucleotide mixtures I and II in the subsequent hybridizations (see Table III).

In another step, chromosomal DNA is isolated from Acinetobacter calcoaceticus microorganisms (strain No. 30008) cultured in a suitable culture medium. The chromosomal DNA is then cleaved with the restriction endonucleases Bcl I, EcoRI and Hind III, blotted onto nitrocellulose, and hybridized with the oligonucleotide mixtures I and II. This entails a Bcl I DNA fragment 6400 bp in size hybridizing with oligonucleotide mixture I. This fragment is then cloned into the BamHI cleavage site of the plasmid pBR327. Restriction analysis, combined with determination of a part-sequence of the cloned BclI fragment, shows that this fragment codes for the N-terminal region of the mutarotase polypeptide.

A Hind III fragment of the chromosomal DNA of Acinetobacter calcoaceticus (strain No. 30008) which is about 1500 bp in size hybridizes with oligonucleotide mixture II. This fragment is therefore cloned into the Hind III cleavage site of bacteriophage M13mp11. The subsequent mapping and determination of a partial-nucleotide sequence shows that the cloned Hind III fragment codes for the C-terminal region of the mutarotase polypeptide.

Hence the invention relates to the DNA sequence shown in FIG. 10, which codes for a polypeptide having the biological activity of the enzyme mutarotase.

The invention furthermore relates to a recombinant expression plasmid in which the entire coding region of the mutarotase gene is under the control of the $\lambda$-$P_L$ promotor and determines the entire DNA sequence of the mutarotase gene. This DNA fragment coding for the N-terminal region of the mutarotase polypeptide is derived from the abovementioned recombinant pBR327 Clone, and the DNA fragment coding for the C-terminal region of the mutarotase polypeptide is derived from the abovementioned M13mp11 clone. According to the invention, it is equally possible to replace the $\lambda$-$P_L$ promotor as expression control sequence by an E.coli, promotor system such as the E.coli lac system, the E.coli $\beta$-lactamase system, the E. coli trp system or the E.coli lipoprotein promotor, a yeast expression control sequence, or another eukaryotic expression control sequence. The only important points in this context are that the gene is functionally linked to the expression control sequence, and that the expression control sequence chosen is suitable for a particular host organism.

The invention particularly relates to the expression plasmid pWH 1372 which contains the DNA sequence which codes according to the invention for the mutarotase polypeptide.

After the recombinant expression vector has been constructed, it is introduced in a customary manner into a transformable host organism, for example an E.coli bacteria such as, for example, E.coli strain No. 69 (E.coli K12 $\Delta$H1). The transformed host organism is then cultivated in a manner known per set in a suitable nutrient medium, and the polypeptide having the biological activity of the enzyme mutarotase, which is formed on expression, is obtained therefrom by standard methods.

Thus the invention relates to the polypeptide which is synthesized on expression under the said conditions, has the biological activity of mutarotase and has the amino acid sequence shown in FIG. 11. The invention also relates to the host organism containing the DNA according to the invention, in particular E.coli WH1372 into which the plasmid pWH1372 has been transformed.

It is possible according to the invention, by use of the isolated DNA sequence, which codes for mutarotase, from Acinetobacter calcoaceticus as a probe molecule in gene banks of mutarotase-forming microorganisms or mammals, to identify the relevant mutarotase gene and to isolate it from these gene banks. It is possible in this way, by functional connection of the mutarotase-coding sequences of these organisms with suitable expression control sequences, also to prepare polypeptides having the biological activity of the enzyme mutarotase from mammals, such as cattle and pigs, and microorganisms, for example of the genus Aspergillus, in any desired amount. The polypeptide having the biological activity of the enzyme mutarotase which is prepared by the process according to the invention is characterized by, for example, the following properties. The molecular weight is about 40,000. The pH activity optimum is in the pH range 7 to 8, and the temperature optimum is 42° C. to 46° C. The Michaelis constant for glucose is 6 to 8 mM.

The activity is approximately halved by $Hg^{++}$ and $Fe^{+++}$ ions at concentrations of 2 mM; inhibition by $Cu^{++}$, $Co^{+++}$ and $Zn^{++}$ ions is complete at the same concentration.

The polypeptide having the biological activity of the enzyme mutarotase which is prepared according to the invention is specific for aldohexoses. The activity is determined as follows:

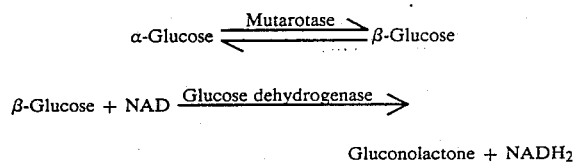

$$\alpha\text{-Glucose} \xrightleftharpoons{\text{Mutarotase}} \beta\text{-Glucose}$$

$$\beta\text{-Glucose} + NAD \xrightarrow{\text{Glucose dehydrogenase}}$$

$$\text{Gluconolactone} + NADH_2$$

Mutarotase, glucose dehydrogenase and NAD are allowed to react with a freshly prepared solution of $\alpha$-glucose, and the $NADH_2$ which is formed is determined by measurement of the extinction at 366 nm. Measurement of the increase in the rate of $NADH_2$ formation by mutarotase in relation to a reference figure allows calculation of the mutarotase activity of the solution used.

Thus, the mutarotase activity is determined in a manner known per se via glucose dehydrogenase determination. The latter is one of the standard methods in, for example, clinical chemistry.

The mutarotase enzyme activity is found from the difference between the blank (containing no mutarotase) and the analytical figure (containing mutarotase) by the following formula:

Enzyme activity = $\Delta\Delta E/\min. \times 4.09$ U of mutarotase per ml of enzyme solution used. (E = extinction at 366 nm)

Crude mutarotase samples must be tested for absence of glucose, because any $\beta$-glucose which is introduced interferes with the assay.

All the restriction enzymes and the starting plasmid, phage and host systems which are used for cloning and which are mentioned heretofore and hereinafter are, when no details are given of their origin or preparation in the descriptive text, known or described in detail in the reference literature and thus readily accessible. Furthermore, a detailed review of these and of some of the standard methods used is to be found in (34).

The figures in which the individual parts of the invention are depicted in an illustrative form are explained below.

FIG. 1: Purification of mutarotase. The purification is monitored by SDS gel electrophoresis after the individual purification steps.

Lane 1: crude extract;
Lane 2: after chromatography on Sephadex G100;
Lane 3: after chromatography on CM-Sephadex;
Lane 4: after chromatography on hydroxyapatite;
Lane 5: molecular weight standard.

Figure 2:
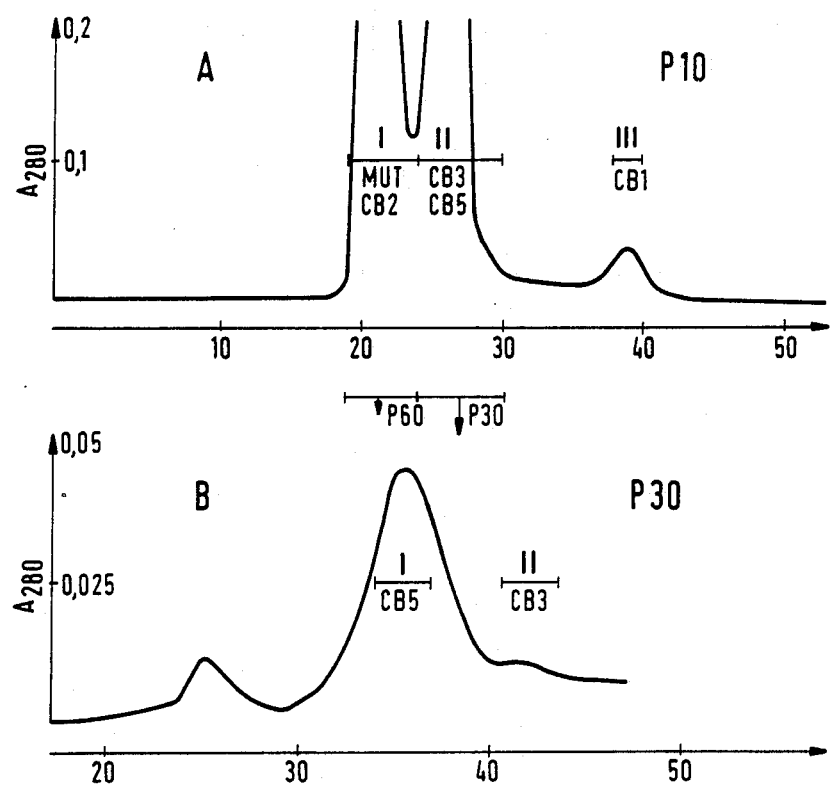

FIG. 2: Separation of the cyanogen bromide fragments by gel filtration through Biogel-B10 and -P30. Mut indicates uncleaved material, and CB1-5 indicates the sequence of the cyanogen bromide fragments within the protein. CB4 has 11 amino acids (see FIG. 4) and is thus too small to be detected on elution.

Figure 3:
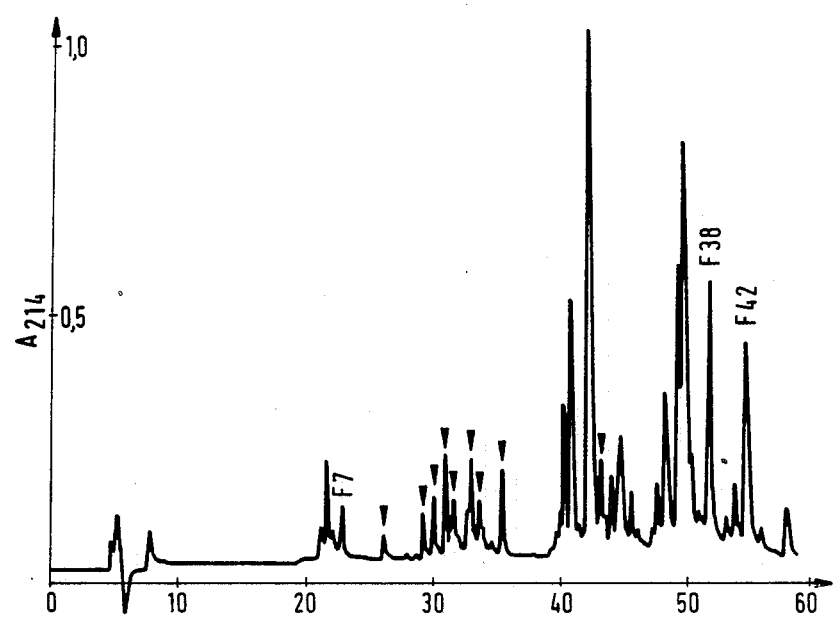

FIG. 3: Separation of the peptides from trypsin cleavage by reversed phase high-pressure liquid chromatography.

Figure 3A:
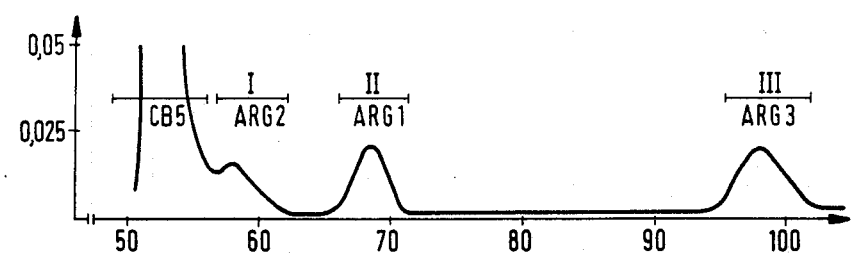

FIG. 3a: Elution chromatogram of the ARG C fragments of CB5 on a P10 column.

FIG. 4: Sequencing strategy for the mutarotase polypeptide and partial polypeptide sequence. The amino acids are indicated by the single-letter code. "*" indicates positions where the amino acids were undefined. Peptides produced by cleavage with cyanogen bromide, trypsin or endoproteinase ARG C were called CB, F or ARG. The location of F42 was not determined until the structural gene had been sequenced.

Figure 5:
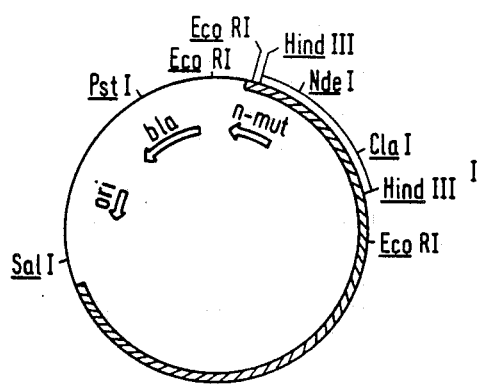
Figure 5:
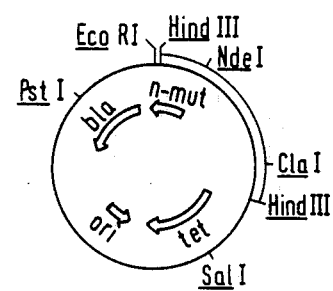

FIG. 5: Restriction maps of the recombinant plasmids pWH1318 and pWH1319. The recombinant plasmid pWH1319 was obtained by insertion of the Hind III fragment from pWH1318, which is 1500 bp in size and contains the N-terminal part of the structural gene, into pBR322.

FIG. 6a: The unshaded zone shows the same region as the unshaded zone in FIG. 5a (plasmid pWH1319). The arrow shows the 5'-3' direction of the mutarotase gene. This region contains the Hind III fragment which is 1500 bp in size and hybridizes with oligonucleotide mixture I.

FIG. 6b: This depicts the Hind III fragment which is 1500 bp in size and is downstream of the Hind III cleavage site which is located proximal to the BclI cleavage site, and which on analysis of the genomic DNA (total DNA blot) hybridizes with oligonucleotide mixture II. The region which is underlined shows the overlap with the DNA fragment depicted in FIG. 6a. The two depicted DNA fragments hybridize together because of this overlapping region.

Figure 7:
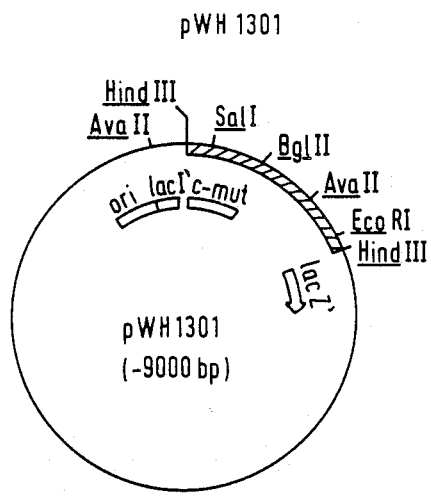

FIG. 7: Restriction map of the M13mp11 clone pWH1301.

Figure 8:
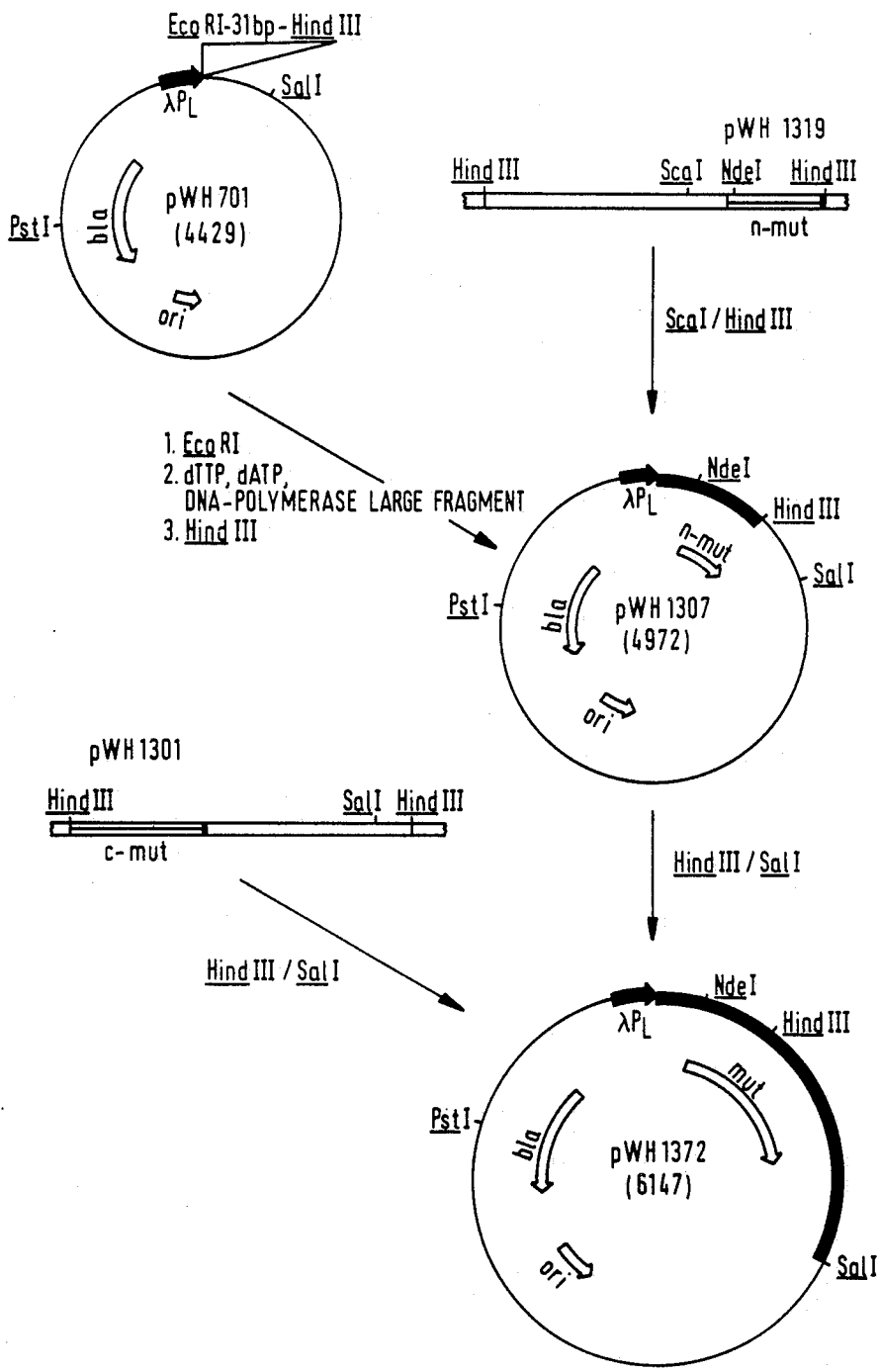

FIG. 8: Diagram of the construction of the recombinant expression plasmid pWH1372.

Figure 9:
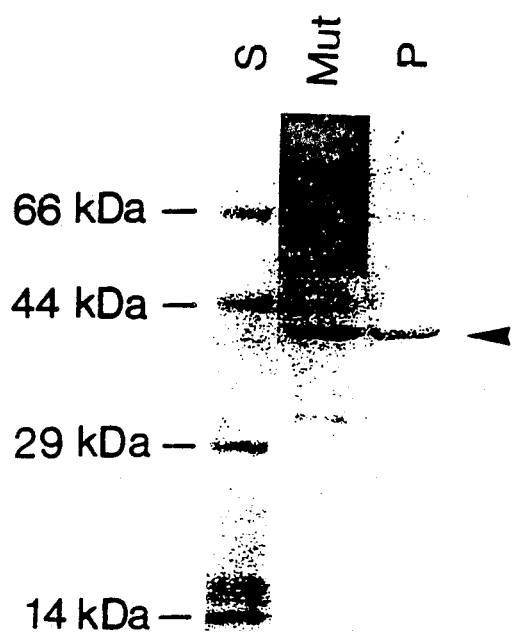

FIG. 9: Working up of the polypeptide having the biological activity of the enzyme mutarotase from the medium. A single chromatographic step results in a purity such that no impurities whatever are detectable in the mutarotase on a SDS gel.
  Lane "Mut": after $(NH_4)_2SO_4$ precipitation from the medium;
  Lane "P": after chromatography on CM-Sephadex
  Lane "S": standard calibration proteins.

FIG. 10: DNA sequence of the mutarotase gene from Acinetobacter calcoaceticus (DSM 30008).

FIG. 11: Amino acid sequence of the product of expression of pWH1372.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight; unless otherwise indicated.

The examples which follow illustrate the invention. The following abbreviations are used in them:
  ATP adenosine triphosphate
  Bis N,N,N',N'-methylenebisacrylamide
  bp base pairs
  BSA bovine serum albumin
  CB peptides produced by cyanogen bromide cleavage
  cpm counts per minute
  D Dalton, g/mol
  DMSO dimethyl sulfoxide
  dNTP deoxynucleoside 5'-triphosphate
  EDTA ethylenediaminetetraacetate
  *E.coli Escherichia coli*
  HPLC high-pressure liquid chromatography
  IPTG isopropyl thiogalactoside
  $32_P$ phosphorus isotope of relative mass 32
  PEG polyethylene glycol
  PVP polyvinylpyrrolidone
  ARG peptides produced by cleavage with endoproteinase ARG C
  rpm revolutions per minute
  SDS sodium dodecyl sulfate
  F peptides produced by cleavage with trypsin
  Tris trishydroxymethylaminomethane
  Tryptone casein cleaved with trypsin
  U unit of enzyme activity
  UV ultraviolet
  X-GAL  5-bromo-4-chloro-3-indolyl  β-D-galactopyranoside
  A,T,C,G nucleotides: adenine, thymine, cytosine, guanine

EXAMPLE 1

Isolation and purification of mutarotase from Acinetobacter calcoaceticus

A fermenter is first charged with 100 liters of a sterile nutrient medium of the following composition:
  peptone from casein 0.5%
  yeast extract 1.0%
  maize starch powder 0.3%
  dipotassium hydrogen phosphate 0.8%
  magnesium sulfate heptahydrate 0.04%
  glucose 1.2%
  silicone antifoam 10 ml
  pH 6.8

The fermenter which has thus been prepared is inoculated with 1 liter of a submerged culture of Acinetobacter calcoaceticus strain 30008 which has been prepared in the same nutrient solution with incubation for 18 hours.

This culture is incubated at 34° C. for 18 hours with moderate aeration.

The biomass, measured as turbidity, increases for the first 2 to 10 hours and then remains constant. After 10 hours the culture has reached the maximum mutarotase activity at 43 U/l.

The following methods are used to liberate the mutarotase from the bacteria and determine the activity: 3 ml of a thoroughly mixed, glucose-free sample from the fermenter are centrifuged at 5,000 rpm for 10 minutes, and the supernatant is discarded. The pellet of bacteria is suspended in 3 ml of 0.1M phosphate buffer, pH 6.5, and 0.1 ml of EDTA solution (1.8 g/l), and the suspension in a centrifuge tube is rapidly frozen in an acetone/dry ice cold bath and then thawed in a waterbath at 40° C. One drop of a detergent and 25 to 30 mg of lysozyme are added (about 15,000 U/mg), and the mixture is stirred at 28° C. for 15 minutes. It is then heated at 45° C. for 5 minutes to inactivate NADH oxidases, disruption is carried out, and the reaction mixture is clarified by centrifugation. Determination of the enzyme in the clear supernatant thus obtained is carried out by the method described above.

When the culture reaches the maximum activity the crude mutarotase extract is prepared. 0.5% of a detergent and 0.1 mol/l potassium chloride are added to 100 liters of bacterial suspension. The cells are disrupted with a high-pressure homogenizer at 500 bar. The bacterial suspension must be cooled during this. The cell detritus is removed in a centrifuge at $3000 \times g$ for 3 hours. The precipitate is discarded, and 20% polyethylene glycol is added to the cloudy centrifugate in order to precipitate concomitant substances. The mixture is then stirred for 30 minutes, and the precipitate is removed by centrifugation. The supernatant, which is still cloudy, contains about 2 U/ml mutarotase and is subjected to diafiltration against water until the conductivity is $3 \times 10^{-3}$ S. After the diafiltration, the mutarotase is adsorbed onto a dry ion exchanger at pH 5.5 in a batch processor. 5 to 10 g of ion exchanger material are necessary for 20,000 U. The loaded ion exchanger is removed by filtration with suction and washed with 0.025M potassium phosphate buffer, pH 5.5, until the filtrate is clear. The loaded ion exchanger is then packed into a column and washed with 0.025M potassium phosphate buffer, pH 5.5, to zero extinction, and then elution is carried out with a potassium chloride gradient.

The enzyme-containing fractions are collected, concentrated by ultrafiltration, and then freeze-dried. The specific activity of the crude extract thus obtained is about 16.1 U/mg of protein.

2420 mg (=34,800 U) of the resulting crude extract are applied to a column of Sephadex G100 molecular sieves ($20 \times 85$ cm). Elution is carried out with 20 mM Tris.HCl, pH 7.2, at a flow rate of 70 ml/hour, collecting fractions of volume 14 ml. The mutarotase activity is found in the eluate fractions. The fractions are combined in such a way that a protein of molecular weight 21 kDa which overlaps on elution is excluded. This is because the latter cannot be removed by the subsequent purification steps.

The combined fractions are applied to a CM-Sephadex column ($2 \times 20$ cm). The loaded column is washed with 250 ml of 20 mM $K_2HPO_4/KH_2PO_4$, pH 9.0. The flow rate is 20 ml/hour, collecting fractions of volume 5 ml. A linear gradient (350 ml of 20 mM and 350 ml of 170 mM $K_2HPO_4/KH_2PO_4$, pH 9.0) is used for elution. Mutarotase is eluted at 80 mM phosphate.

The collected samples are diluted 1:4 and applied to a hydroxyapatite (spherical) column ($4 \times 10$ cm). The flow rate is 9.2 ml/hour, collecting fractions of volume 2.3 ml. The column is washed with 100 ml of 20 mM $K_2HPO_4/KH_2PO_4$, pH 9.0. Elution is carried out with linear gradient from 300 ml of 20 mM $K_2HPO_4/KH_2PO_4$, pH 9.0, to 300 ml of 300 mM $K_2HPO_4/KH_2PO_4$, pH 9.0, the mutarotase being released by the column material at 85 mM.

The purification is followed on an SDS gel (5) (FIG. 1). After the third column step, only one band is now detectable on the gel, corresponding to a molecular weight of 40 kDa. It can be deduced from the migration behavior on the G100 molecular sieve column that, under natural conditions, the protein is in the form of an oligomer.

Table I shows a summary of the purification steps. The Bradford (6) method was used for protein determination.

TABLE I

| Purification scheme for mutarotase | | | |
|---|---|---|---|
| | Activity (U) | Specific acitivity (U/mg) | Yield in % |
| Crude extract | 34800 | 16.5 | 100 |
| Hydroxyapatite | 27885 | 68.0 | 80 |
| CM-Sephadex | 19841 | 107.0 | 57 |
| Hydroxyapatite | 15656 | 233.0 | 45 |

The methods which are described below are used to determine a part-sequence, which contains amino acids which are coded for by the minimum possible number of different codons from the DNA, of the mutarotase peptide. Sequences of this type are especially well suited for subsequent selection of corresponding oligonucleotides (see Example 3).

The protein which, after the final purification step by column chromatography as in Example 1, is in phosphate buffer is mixed with one half the volume of 100 percent acetic acid and one half the volume of n-propanol, and the mixture is evaporated to dryness in a rotary evaporator. To remove salts, the residue is applied to a molecular sieve column ($2.5 \times 25$ cm) and elution is carried out with 70 percent acetic acid. Protein in the individual fractions is detected by measurement of the absorption at 280 nm. Protein-containing fractions are combined and the solution is evaporated to dryness in a rotary evaporator. The protein obtained in this way (mutarotase) was used for the subsequent sequencing of the N-terminal amino acids and for the cyanogen bromide and trypsin cleavages.

Cyanogen bromide, trypsin and endoproteinase ARG C cleavages

The cleavages with cyanogen bromide and with the enzymes trypsin and endoproteinase ARG C are carried out to determine part-sequences of amino acids in mutarotase.

Cleavage with cyanogen bromide is carried out by the procedure of Gross and Wittkopp (12). 15 mg of the protein from which salts have been removed as described above and which has been evaporated to dryness are taken up in 3 ml of 70 percent formic acid, a 100-fold molar excess of cyanogen bromide is added, and the mixture is incubated in the dark for 7 hours. The formic acid is removed in a rotary evaporator, and the residue is taken up in 2 ml of 70 percent acetic acid. The cleavage products are then separated on a P 10 and a P 30 molecular sieve column ($2.5 \times 50$ cm). The individual cleavage products (fragments) are called CB1-5. FIG. 2 shows the fractions in which the individual fragments are eluted in the column chromatography described.

For digestion of the entire protein with trypsin, 2 mg of protein from which salt has been removed and which has been evaporated to dryness are dissolved in 2 ml of 1M ammonium bicarbonate, and one percent by weight of proteinase is added. Because the entire protein does not dissolve under these conditions, the mixture is adjusted to 0.05% in SDS. Trypsin has to be added a total of $4\times$. The last addition is followed by incubation overnight. The reaction mixture, which still contains insolubles, is applied in 100 μl aliquots to an HPLC column.

The Beckman HPLC system comprises two solvent dispensers (models 100 A and 110 A), a variable wavelength detector (model 165) and a gradient mixer. Elution starts with solution A (0.05% trifluoroacetic acid in water) for 10 minutes. Subsequently a gradient is applied, the concentration of solvent B (0.025% trifluoroacetic acid in acetonitrile) increasing to 50% within 50 minutes. The flow rate is 1.6 ml/min and the temperature is 500° C. The column (0.72×25 cm) is packed with silica gel in the form of spheres (Nukleosil 5 C18, Machery & Nagel, Düren). The peptides are identified by measurement of the absorption at 216 nm. For sequencing, the fractions from 7 to 10 chromatography runs are collected.

In this way, inter alia the trypsin fragments F38 and F42 of the entire mutarotase polypeptide are isolated (see FIG. 3).

Digestion of the entire protein with trypsin results in cleavage products which are difficult to separate in some cases.

The separation problem is simplified when cyanogen bromide fragments are used in place of the whole protein in an enzymatic digestion. In order to obtain further information about the C-terminal region of the protein the cyanogen bromide fragment CB5 was cleaved at its arginine positions with endoproteinase ARG C.

The ARG C cleavage likewise takes place in 1M ammonium bicarbonate, pH 7-8, in the presence of 1 percent by weight of the proteinase, at 37° C.

The digestion mixture was evaporated in a rotary evaporator, the residue was dissolved in 2 ml of 90% formic acid, and the solution was diluted with 1 ml of water and applied to a P10 column (2.5×100 cm). Elution was carried out with 20% formic acid.

In this way three fractions I to III were eluted and, of these, fraction I was rechromatographed once more on a P10 column 2.5×50 cm long (FIG. 3a).

Amino acid analyses

An amino acid analysis of the entire mutarotase polypeptide is initially carried out. For this purpose, 5 nmol of protein are hydrolysed under reducing conditions in 2 ml of 6M HCl, 0.05% thioglycol, at 150° C. for 2 hours. Hydrolylsis under oxidizing conditions is carried out in 2 ml of 6M HCl, 1.5% DMSO, at 110° C. for 20 hours. The sample is then evaporated in a rotary evaporator and analysed on a 0.6×21 cm DC 6A resin column in a LC 600 (Biotronik, Frankfurt) amino acid analyser in accordance with the manufacturer's instructions.

The amino acid composition of the entire polypeptide which has thus been determined is shown in Table II. The amino acid composition deduced from the DNA sequence is listed in the "sequence" column. The molecular weight of mutarotase which can be calculated from this is 39,500 Da.

TABLE II

| Amino acid | Oxid. cond. | Red. cond. | Sequence | |
|---|---|---|---|---|
| ASX | 48.56 | 51.71 | 53 | ASN 33 ASP 20 |
| THR | 23.13 | 22.45 | 27 | |
| SER | 19.89 | 18.25 | 23 | |
| GLX | 38.62 | 38.12 | 33 | GLN 25 GLU 8 |
| PRO | 19.57 | 18.78 | 18 | |
| GLY | 36.32 | 38.46 | 33 | |
| ALA | 27.00 | 24.38 | 20 | |
| CYS | | | | |
| VAL | 23.34 | 27.82 | 31 | |
| MET | 4.70 | 4.04 | 4 | |
| ILE | 13.50 | 15.52 | 15 | |
| LEU | 29.30 | 29.88 | 30 | |
| TYR | 13.08 | 13.71 | 15 | |
| PHE | 14.65 | 15.25 | 15 | |

TABLE II-continued

| Amino acid | Oxid. cond. | Red. cond. | Sequence |
|---|---|---|---|
| HIS | 12.66 | 7.01 | 6 |
| LYS | 23.23 | 24.23 | 25 |
| ARG | 11.20 | 9.30 | 9 |
| TRP | ? | 2 | 2 |
| | 359 | 359 | 361 |

Under the said experimental conditions, tryptophan cannot be determined.

It can be seen from Table II that the protein contains four methionine residues. Hence, five fragments are expected on cyanogen bromide cleavage. Thus there is agreement between the results of the cyanogen bromide cleavage and the subsequent separation of the cleavage products, which have been described above (see FIG. 2), and the results of the amino acid analysis (see Table II).

Where appropriate, the amino acid composition of the peptides obtained by cyanogen bromide, trypsin and endoproteinase ARG C cleavage is also determined as described above.

Determination of amino acid sequences

Firstly, the N-terminal amino acids of mutarotase are determined with an automatic liquid-phase sequencing apparatus (Beckman model 890C). The 2-anilino-1,3-thiazolin-5-one derivatives of the amino acids are incubated in 20% trifluoroacetic acid at 55° C. for 30 minutes. The phenylthiohydantoin derivatives are identified in an HPLC system (8).

Subsequently the amino acid sequences of fragments CB1, CB2, F42, CB3, CB4, CB5, F38, ARG1, ARG2 and ARG3 are determined (see FIG. 4).

These fragments are sequenced by the solid-phase technique at 50° C. using an LKB model 4020 apparatus. The C-terminal ends of the fragments are coupled to 3-aminoprdpyl-glass using EDC (1-ethyl-3-(3-diethylaminopropyl)carbodiimide.HCl) (9). The subsequent Edman degradation is carried out by the Laurson procedure (10). The phenylhydantoin derivatives of the amino acids are identified by thin-layer chromatography on Merck HPTLC plates (silica gel 60F G 254) (11).

The amino acid sequences of the said mutarotase fragments which are thus obtained are then assigned their relative positions n the overall amino acid sequence of mutarotase.

This is carried out as follows:

The positions of the cyanogen bromide fragments CB1 and CB2 are evident from the agreement between their amino acid sequences and the N-terminal amino acid sequences of the entire polypeptide (see FIG. 4).

The first five amino acids of cyanogen bromide fragment CB3 are determined. The material of the first absorption maximum from the chromatography following the cyanogen bromide cleavage is rechromatographed on a P60 column (2.5×50 cm). Sequencing shows, in parallel, the N-terminal sequence (that is to say the maximum contained uncleaved material) and the first six amino acids of cyanogen bromide fragment CB2. The relative position of CB3 in the mutarotase polypeptide cannot be established until the DNA sequence of the corresponding structural-gene has been determined (see FIG. 4).

The sequence of cyanogen bromide fragment CB4 is completely retained in fragment F 38 from trypsin cleavage. It comprises eleven amino acids (see FIG. 4).

Cyanogen bromide fragment CB5 can be separated from cyanogen bromide fragment CB3 by rechromatography on a P30 column 2.5×50 cm in size. Since no homoserine is found on amino acid analysis, cyanogen bromide fragment CB5 must be the C-terminal fragment. 42 amino acids of CB5 are sequenced (see FIG. 4).

The relative assignment of the established sequences of cyanogen bromide fragments CB4 and CB5 in the entire polypeptide sequence of mutarotase is determined by sequencing fragments from trypsin cleavage of the mutarotase polypeptide and of the cyanogen bromide fragment CB5 of the mutarotase polypeptide.

Fractions I, II and III (FIG. 3a) resulting from subfragmentation of cyanogen bromide fragment CB5 have been sequenced. The sequence of the peptide in fraction II is identical to the first 20 amino acids of CB5.

The peptides were numbered from ARG1 to ARG3 according to their sequence within the cyanogen bromide fragment. The sequence of the peptide in fraction II (ARG1) was identical to the first 20 amino acids of CB5. The peptide from fraction I was identified as ARG2 because its sequence overlapped with positions 21 to 42 of CB5.

In addition to this sequence it had the amino acids Ser-Thr-Arg. ARG3 is the C-terminal sequence of CB5. The sequences of ARG1, ARG2 and ARG3 are shown in FIG. 4.

Because the cyanogen bromide fragment CB5 is the C-terminal peptide fragment of mutarotase, this establishes the C-terminal amino acid sequence of the mutarotase polypeptide (see FIG. 4).

Sequencing of 25 amino acids of the fragment F38 from trypsin cleavage of the entire protein provides the relative positions of the cyanogen bromide fragments CB4 and CB5. Since F38 overlaps with CB4 and CB5, CB4 and CB5 must be directly adjacent (see FIG. 4).

Finally, the amino acid sequence of the fragment F42 derived from the entire mutarotase polypeptide by trypsin cleavage is determined. The relative position of the sequence, which is 25 amino acids long, cannot be established until a nucleotide part-sequence of the mutarotase structural gene has been determined (see Table V).

EXAMPLE 3

Synthesis of oligonucleotides

The gene coding for mutarotase is isolated from a gene bank as described in Example 5.

Oligodeoxynucleotides (abbreviated to oligonucleotides) are prepared by chemical synthesis to act as probe molecules for scanning this gene bank.

The sequence of these oligonucleotides is deduced from amino acids 12 to 17 and 353 to 359 (the last 7 amino acids) of the partial amino acid sequence of the mutarotase polypeptide determined as in Example 2.

Since the genetic code is degenerate, it is necessary to synthesize a variety of oligonucleotides which code for the same amino acid sequence. The oligonucleotides relevant in each case, are listed in Table III.

TABLE III

| | Oligonucleotide mixture I | | | | | |
|---|---|---|---|---|---|---|
| Position in the mutarotase polypeptide | 12 | 13 | 14 | 15 | 16 | 17 |
| Three-letter code | GLN | ASN | GLY | GLN | LYS | VAL |
| Single-letter code | Q | N | G | Q | K | V |
| Oligonucleotide sequence | $CA_A^G$ | $AA_T^C$ | GGT | $CA_A^G$ | $AA_A^G$ | GG |

| | Oligonucleotide mixture II | | | | | | |
|---|---|---|---|---|---|---|---|
| Position in the mutarotase polypeptide | 353 | 354 | 355 | 356 | 357 | 358 | 359 |
| Three-letter code | PHE | LYS | PHE | GLY | VAL | GLN | LYS |
| Single-letter code | F | K | F | G | V | Q | K |
| Oligonucleotide sequence | $TT_C^T$ | $AA_A^G$ | $TT_C^T$ | GGT | GTT | $CA_A^G$ | $AA_A^G$ |

The three-letter code and the single-letter code are the normal abbreviations for the 20 biogenic amino acids which occur in nature.

All the combinations of oligonucleotide sequences shown in Table III are synthesized simultaneously. The synthesis is carried out on a support comprising silica gel provided with functional n-propylamino groups using the phosphoramidite method developed by Caruthers et al. (14, 15). When it is possible to have in the third position of the individual triplets two nucleotides which are unable to form hydrogen bonds with one another, equimolar amounts of the phosphoramidites are made available for the coupling. When the alternatives inserted are G and C or A and T, the support material is divided for this particular coupling step. At the end of the synthesis, the detritylation step is not carried out because the desired oligonucleotide can be more clearly distinguished from byproducts by the trityl protective group at the 5'-end. After the phosphate protecting group has been eliminated, the covalent bond to the support material is hydrolysed, and the base protecting groups are eliminated. The solution is then evaporated to dryness in a rotary evaporator, and the residue is taken up in a buffer (10 mM Tris.HCl, pH 8.0, 1 mM EDTA). Suspended matter and residues of support are removed by centrifugation from the crude mixture of oligonucleotides thus obtained. 5 to 15 $A_{260}$ units are purified in each run through an HPLC column. Elution in this column chromatography starts with solution A (20% acetonitrile in 0.1M triethylammonium acetate) for 5 minutes. Then a gradient is applied, the acetonitrile concentration increasing to 30% within 30 minutes. The flow rate is 15 ml/min and the temperature is 45° C. The eluates containing oligonucleotides are combined and evaporated to dryness, 400 μl of 80 percent (v/v) acetic acid are added and, after 5 minutes at room temperature, the mixture is evaporated to dryness The residue is resuspended in 500 μl of water and rechromatographed with a gradient from 5% to 20% acetonitrile. In this chromatography, the detritylated oligonucleotides are eluted at an acetonitrile concentration between 13 and 17 percent.

Finally, the final yield is determined at 260 nm with HPLC buffer as reference, and the two oligonucleotide mixtures I and II obtained are freeze-dried twice from water and suspended in 10 mm Tris.HCl, pH 8.0, 0.1 mM EDTA buffer.

EXAMPLE 4

Preparation of chromosomal DNA from acinetobacter calcoaceticus

Cells of Acinetobacter calcoaceticus (DSM 30008) are cultured as in Example 1.

5 g of cells were suspended in 50 mM NaCl, 50 mM EDTA, 30 mM Tris.HCl, pH 7.9, and incubated with 200 mg of lysozyme at 37° C. for 30 minutes. The suspension is adjusted to a concentration of 1% in SDS, and is incubated with 5 mg of proteinase K (Merck) at 37° C. for a further 30 minutes. The mixture is then extracted carefully with phenol (equilibrated with 10 mM Tris.HCl, pH 8.0, 0.1 mM EDTA) six times, and then with chloroform/isoamyl alcohol (20:1) four times.

The resulting DNA is then precipitated by addition of three times the volume of ethanol. The DNA is centrifuged down, and the sediment is dried and resuspended in 5 ml of 10 mM Tris.HCl, pH 8.0, 0.1 mM EDTA. Then 50 μg of DNase-free RNase A (Sigma) are added. The DNase has previously been inactivated by boiling in 100 mM NaOAc, pH 5.5, for 10 minutes. After incubation with RNase A for 30 minutes, 250 μg of proteinase K are added, and the mixture is incubated for a further 30 minutes. It is then again extracted again by shaking with phenol six times and diethyl ether three times. The DNA is then precipitated by addition of half the volume of a 30 percent PEG solution in 1.5M NaCl, washed with ethanol and dried in a desiccator.

EXAMPLE 5

Cloning of genomic mutarotase sequences

Material and methods

Enzymes: Restriction enzymes, T4 DNA ligase and E.coli polymerase and the Klenow fragment of E.coli polymerase were bought from Boehring, BRL or Biolabs and used in accordance with the manufacturer's instructions. Eco RI is prepared by a procedure of Greene et al. (16).

Gel electrophoreses: For restriction analyses DNA fragments of a length up to 100 bp are fractionated on 5% polyacrylamide gels (acrylamide/bisacrylamide 20:1) in TEB buffer (60 mM Tris, 60 mM boric acid, 1 mM EDTA, pH 8.3) and 10% glycerol (17). For the fractionation of DNA fragments of a length between 500 bp and 9,000 bp, use is made of 1% agarose gels in TAE buffer (40 mM Tris, 15 mM NaOAc, 1.25 mM EDTA, pH 8.3) (18). For vertical agarose gel electrophoreses, a 3 cm-high 8% polyacrylamide supporting block is cast in the lower part of the apparatus. Since DNA isolated from agarose gels is not suitable for cloning experiments, for preparative purposes use is made of a 3% polyacrylamide gel (acrylamide/bisacrylamide 50:1) to which no glycerol has been added. After the gel electrophoresis, the gels are removed from the apparatus and stained in a 0.001 percent ethidium bromide solution for 10 minutes. This makes the DNA-containing bands visible under UV light.

Preparation of DNA: The preparation of chromosomal DNA from Acinetobacter calcoaceticus is described in Example 4.

The isolation of plasmid DNA and of DNA of the replicative form of the M13 phage is carried out by the method of Hardies et al. (19). The single-stranded M13 DNA is prepared as described by Messing (20). For fractionations by gel electrophoresis or hybridization analyses, the phage supernatants are concentrated fivefold by precipitation with ¼ the volume of 20 percent PEG 6000 solution in 2.5M NaCl at 4° C. for 15 minutes.

The preparative isolation of plasmid DNA is carried out by the procedure for rapid analysis of transformants as follows.

Single colonies of bacteria are plated out on a selection plate. Using an inoculating loop, about 1 mm³ of bacterial aggregate is removed and suspended in 80 μl of triton buffer (8% sucrose, 5% Triton X100, 50 mM EDTA, 50 mM Tris.HCl, pH 8.0). After addition of 7 μl of lysozyme buffer (10 mg/ml lysozyme in 50 mM Tris.HCl, pH 8.0, 50 mM EDTA), the samples are incubated at room temperature for 5 minutes. They are then heated at 100° C. for 40 seconds and subsequently placed on ice for 2 minutes. After centrifugation in a microcentrifuge for 15 minutes, the viscid residues of the bacteria are removed with an inoculating loop. Then 80 μl of isopropanol are added to the supernatant, and the mixture is placed in an icebath for 20 minutes. The precipitate which is produced by this is sedimented by centrifugation for 15 minutes and, after the supernatant has been discarded, it is washed twice with 600 μl of ethanol and dried in vacuo. The resulting plasmid DNA is dissolved in 40 μl of TE buffer (10 mM Tris. HCl, pH 8.0, 0.1 mM EDTA) and analysed on an agarose gel. Elution of the gels:

The elution of DNA fragments from polyacrylamide gels is carried out by the method of Maxam and Gilbert (21). Pieces of 5 percent and 20 percent polyacrylamide gels are first mechanically comminuted using a Teflon rod. Pieces of 3 percent polyacrylamide gel are forced through a cannula with a diameter of 0.8 mm using a disposable 20 ml syringe.

The eluted DNA is applied to a DE 52 column with a volume of 200 pl of column material, and is eluted with 400 μl of 2M NaCl (20). Oligonucleotides are eluted with 1M NaCl and are then used directly for hybridization. After elution from the DE 52 column, double-stranded DNA is precipitated twice with ethanol. Transformation:

E.coli strains are transformed by the CaCl$_2$ method (17).

Radiolabelling of DNA:

Oligonucleotides are radiolabelled at their 5'-ends using T4-polynucleotide kinase and [γ-$^{32}$P]-ATP (2%). The [γ-$^{32}$P]-ATP having a specific activity of 8,000 Ci/mmol which is required for this is synthesized by the method of Walseth and Johnson (23). The specific activity of the resulting labelled oligonucleotides is increased by the removal of non-phosphorylated oligonucleotides on a 40 cm-long 20 percent 8M urea gel. This gel electrophoresis also removes free ATP and inorganic phosphate.

Plasmid DNA is radio labelled by the nick translation method of Weinstock (24). Excess triphosphates remaining in the reaction mixture are then removed over a G50 molecular sieve column in a Pasteur pipette.

Hybridization:

Southern blot analysis:

The restriction fragments obtained by cleavage of chromosomal DNA or of DNA from recombinant plasmids are separated on agarose gels and blotted onto nitrocellulose by the Southern (25) method. The nitrocellulose filter is sealed into kitchen film and prehybridized with 1 ml of hybridization solution per 40 cm² of filter surface area at 60° C. for 4 hours (6×NET, 10×Denhardt solution, 0.1% SDS; 1×NET=0.15M NaCl, 15 mM Tris.HCl, pH 8.3, 1 mM EDTA; 1×Denhardt solution=0.02% bovine serum albumin, 0.02% polyvinylpyrrolidone 40, 0.02% Ficoll). Then the labelled oligonucleotide (about $1-2\times 10^6$ cpm by Cerenkov counting) is added. The hybridization temperature chosen for both oligonucleotide mixtures is 40° C. After hybridization for 3 to 5 hours, the filters are washed twice for 15 minutes at 4° C. They are then washed at 40° C. for 1 minute. The subsequent autoradiography is then carried out at $-70°$ C. for 12 hours. Unspecific hybridization signals can be eliminated by a further 1minute washing procedure at elevated temperature. The relevant nitrocellulose filters are then exposed once more as described above. Dot-blot analysis:

The DNA from recombinant plasmids which has been prepared as described above, the chromosomal DNA eluted from 3 percent polyacrylamide gels, and single-stranded phage supernatants are subjected to dot-blot analysis. For this purpose, 5 μl of DNA are pipetted onto a nitrocellulose filter and dried on with an air-blower. In the case of double-stranded DNA, the filter is further treated on moistened chromatography paper at room temperature. The following solutions, with which the chromatography paper has been impregnated, are used successively:

5 minutes 250 mM Tris.HCl, pH 7.5; 5 minutes 500 mM NaOH; 5 minutes 500 mM NaOH/1.5M NaCl; 2×2 minutes 1M Tris.HCl, pH 7.5; 4 minutes 500 mM Tris.HCl, pH 7.5/1.5M NaCl; 5 minutes 6×SSC buffer (1×SSC=150 mM NaCl, 15 mM trisodium citrate). The filter is then baked at 80° C. in an oven under reduced pressure for 2 hours. The hybridization of the filters with the radiolabelled oligonucleotide mixtures I and II is carried out as described above. The hybridization of the filters with nicktranslated plasmids is carried out by the procedure of Wahl et al. (26). Colony hybridization:

Each of two agar plates (enriched with 40 mg/liters ampicillin) (24.3×24.3 cm, Nunc Intermed, screening plate) is covered with a nitrocellulose filter (Schleicher and Schüll BA-85). 1,000 bacterial colonies are then transferred, using sterile toothpicks, in the same pattern to the nitrocellulose filter of one plate and the agar of the other plate and are incubated at 37° C. for 18 hours. The filters with the colonies are then treated in analogy to the dot-blot analysis procedure (see above). After the filters have been baked at 80° C. under reduced pressure for 2 hours, they are washed three times with 6×NET, 10×Denhardt solution, 0.1% SDS and hybridized in the same buffer with $24\times 10^6$ cpm of labelled oligonucleotides at 40° C. for 5 hours. The filters are subsequently washed twice for 15 minutes with 6×SSC at 4° C., then at 40° C. for 5 to 8 minutes and finally at 42° C. for 1 minute. After the first exposure of an X-ray film, the filters are washed again, with 6×SSC at 44° C. for 2 minutes, and used for exposure of another X-ray film. Finally, the filters are washed in 6×SSC at 46° C. for 1 minute and used again for exposure of an X-ray film. Sequence analyses:

For the most part, DNA sequences are determined by the method of Maxam and Gilbert (21). Where appropriate, for example when no suitable restriction cleavage sites were present, the DNA fragments are subcloned into pUR250 (28). For the identification of M13 clones a sequencing by the M13 method (27) is carried out.

The said methods are essentially standard methods of molecular biology and are described in laboratory manuals such as "Molecular Cloning, A Laboratory Manual", by T. Maniatis et al., Cold Spring Harbor Laboratory, 1982.

Cloning of genomic mutarotase sequences:

400 μg samples of chromosomal DNA from Acinetobacter calcoaceticus (DSM 30008) are cleaved with the restriction endonucleases Eco RI, Hind III and Bcl I. Then 20 μg are electrophoresed on a 1 percent agarose gel and blotted onto nitrocellulose (so-called total DNA blot). After the hybridization has been carried out as described above, washing is carried out a second time at 44° C. for oligonucleotide mixture I, and a second time at 46° C. for oligonucleotide mixture II.

Hybridization of the Bcl I cleavage with oligonucleotide mixture I results in reproducible signals in the region of 6400 bp in size. Reproducible signals in the region of 2000 bp in size result on hybridization of the Eco RI cleavage with oligonucleotide mixture I, and in the region of 1500 bp in size with the Hind III cleavage.

A Hind III fragment which is about 1500 bp in size hybridizes with oligonucleotide mixture II.

Subsequently a gene bank is constructed with the Bcl I fragment of Acinetobacter calcoaceticus DNA and the Bam HI-cleaved DNA of the plasmid pBR327 (ATCC 31344).

For this purpose, 120 μg of BclI-cleaved chromosomal DNA from Acinetobacter calcoaceticus are electrophoresed on a 3 percent polyacrylamide gel until fragments of a length of 3800 bp have reached the lower edge of the gel. The acrylamide above 3800 bp is cut into 9 narrow strips, and the DNA is eluted from each individual gel fraction. ¼ of each of the eluted DNAs is hybridized in a dot-blot analysis. The fraction from the gel strip with the second largest fragments results in the strongest signal. For this reason, 1/10 of the eluted DNA of this fraction is ligated with 200 ng of pBR 327 plasmid DNA which has been cleaved with Bam HI and dephosphorylated (29). Subsequent transformation of E.coli RRI (30) results in 3000 tetracycline-sensitive colonies. 1000 of these colonies are examined by the colony hybridization method described above.

Then plasmid DNA from 25 colonies which have resulted in the strongest signals on colony hybridization are isolated as described above and subjected to dot-blot analysis.

10 of the 25 examined plasmids result in positive signals. Hence, for subsequent experiments DNA from 6 of the plasmids resulting in positive signals is isolated from 250 ml cultures. An Eco RI and a Hind III Cleavage are carried out with each of the plasmids, fractionating on an agarose gel.

The DNA is fixed to nitrocellulose by the Southern method and hybridized with radiolabelled oligonucleotide mixture I. The washing temperature in three 1-minute steps is increased to 52° C. At this temperature, there is hybridization only of an Eco RI fragment, 2000 bp in size, and of a Hind III fragment, 1500 bp in size, of a plasmid which is called pWH 1318. The sizes of these fragments agree with the results of the hybridization with total chromosomal DNA.

There is no positive signal on hybridization with oligonucleotide mixture II.

FIG. 5a shows a restriction map of the recombinant plasmid pWH 1318 obtained by cleavage with the appropriate restriction nucleases.

The recombinant plasmid pWH 1319 is obtained by cloning the Hind III fragment, 1500 bp in size, from pWH 1318 into the Hind III cleavage site of the plasmid pBR 322 (31) (see FIG. 5).

Starting from the NdeI cleavage site of the plasmid pWH 1319, initial sequencing of the insertion is carried out by the Maxam and Gilbert method (21).

The DNA sequence thus obtained shows complete agreement with the first 18 amino acids of the mutarotase polypeptide (see Table IV and FIG. 4):

TABLE IV

| Ala | Thr | Leu | Asn | Val | | Thr | Thr | Gln | Asn | Gly | Gln | Lys | Val | Asp |
|-----|-----|-----|-----|-----|-----|-----|-----|-----|-----|-----|-----|-----|-----|-----|
| GCA | ACG | TTA | AAT | GTA | ⟵ NdeI ⟶ | ACG | ACT | CAA | AAT | GGC | CAA | AAA | GTT | GAT |
| | | | | | | CA$^G_A$ | AA$^C_T$ | GGT | CA$^G_A$ | AA$^G_A$ | GT | | | |

| Leu | Tyr | Thr | Met | Ser | Asn | Asn | Asn | Gly |
|-----|-----|-----|-----|-----|-----|-----|-----|-----|
| CTA | TAC | ACC | ATG | AGT | AAT | AAC | AAT | GGA |

Hence the results of the sequencing show that the recombinant plasmid pWH 1318 isolated from the gene bank contains: a DNA sequence which codes for the N-terminal region of the mutarotase polypeptide.

The plasmid pWH 1318 cannot contain a DNA sequence coding for one C-terminal region of the mutarotase polypeptide because this plasmid does not hybridize with oligonucleotide mixture II. For this reason, a Hind III fragment, which is 1500 bp in size and hybridizes with oligonucleotide mixture II and with the region, which is about 125 bp in length, contained in the recombinant plasmid pWH 1318 between the Hind III and Bcl I cleavage sites, from the total DNA of Acinetobacter calcoaceticus is cloned (see FIGS. 6a and b).

200 μg of Hind III-cleaved chromosomal DNA are fractionated on a 3 percent polyacrylamide gel. The DNA in the region around 1500 bp in size is eluted. ¼ of the DNA is fixed to nitrocellulose as described above. The fraction hybridizes both with oligonucleotide mixture II and with DNA of the plasmid pWH 1318.

200 ng of the Hind III-cleaved chromosomal DNA from the isolated fraction are ligated with 200 ng of Hind III-cleaved, dephosphorylated M13mp11 RF DNA. The resulting ligation products are used to transform competent E. coli BMH 71-18 which are plated out in soft agar containing IPTG and X-GAL. The transformation is repeated several times. Finally, 541 recombinant phages (white plaques) are present.

1 ml-cultures of E.coli BMH71-18 are infected with 5 plaques each. The precipitated phage supernatants are hybridized with oligonucleotide mixture II and with DNA of the recombinant plasmid pwH 1318. 2 of the 131 phage supernatants show positive signals with both probe molecules. The phages are prepared individually in their replicative form (double-stranded DNA) from a culture with a volume of 2 liters. Restriction analysis of the recombinant phage DNAs shows that both positive M13 clones contain the same insertion with the Eco RI cleavage site at the expected position (FIG. 7). One of these two M13 clones is used for subsequent experiments and is called pWH1301.

DNA sequencing of pWH1301 by the M13 method (27) shows an open reading frame which agrees with the peptide sequence of fragment F42 from trypsin cleavage (Table V).

TABLE V

Part-sequence of the M13 clone pWH1301

| K | T | D | Q | P | T | V | V | N | L | T | N | H | S |
|---|---|---|---|---|---|---|---|---|---|---|---|---|---|
| Lys | Thr | Asp | Gln | Pre | Thr | Val | Val | Asn | Leu | Thr | Asn | His | Ser |
| AAA | ACT | GAT | CAG | CCT | ACA | GTC | GTC | AAC | CTT | ACC | AAC | CAC | AGT |

Hind III —25 bp— Eco RI —30 bp— BclI

| Y | F | N | L | S | G | A | G | N | N | P |
|---|---|---|---|---|---|---|---|---|---|---|
| Tyr | Phe | Asn | Leu | Ser | Gly | Ala | Gly | Asn | Asn | Pro |
| TAT | TTC | AAC | TTA | TCA | GGT | GCT | GGG | AAC | AAT | CCT |

The sequencing results confirm the restriction map postulated for the mutarotase gene in FIGS. 6a and 6b, since the sequence which is found in fact contains a BclI cleavage site (see Table V).

Figure 6:
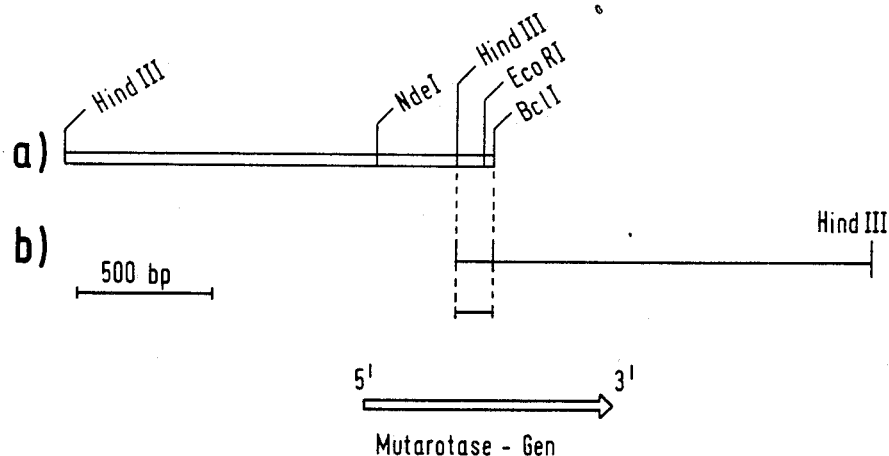

Thus, the clones pWH1318 and pWH1319, and pWH1301, contain overall the complete mutarotase gene from Acinetobacter calcoaceticus (DSM 30008) (see FIGS. 5, 6 and 7).

EXAMPLE 6

Construction of an expression plasmid which contains the entire sequence of the mutarotase gene The expression plasmid used is plasmid pWH701. This is a readily accessible derivative of the plasmid pPLc236 (32) in which the polylinker from the plasmid pUR250 (28) is inserted between the Eco RI and the Hind III cleavage sites. The plasmid pWH701 contains the strong λ-$P_L$ promotor (see FIG. 8, black arrow).

All the subsequent cloning steps are carried out in the host bacterium E.coli W6 (32) in which the λ-$P_L$ promotor is repressed by the $c_I$ repressor. pPLc236, the λ-$P_L$ promotor and host bacterium E.coli W6 are also disclosed in European Patent Application No. 0,041,767. 20 μg of DNA from the recombinant plasmid pWH1319 are cleaved with the restriction endonucleases Hind III and Sca I and electrophoresed on a 5 percent polyacrylamide gel. Subsequently a fragment 574 bp in size is eluted from the polyacrylamide gel.

10 μg of DNA from the expression plasmid pWH701 are cleaved with the restriction endonuclease Eco RI, and the protruding ends are filled in with Klenow polymerase in the presence of dATP and dTTP. After the Klenow polymerase has been inactivated by heating the reaction mixture at 90° C. for 5 minutes and after subsequent ethanol precipitation, the DNA thus obtained is then cleaved with the restriction endonuclease Hind III. The fragment 31 bp in size obtained in this cleavage is removed by electrophoresis on a 3 percent polyacrylamide gel.

200 ng of plasmid DNA prepared in this way and 200 ng of the DNA fragment, 574 bp in size, which has been isolated as described above are ligated together and used for transformation of E.coli W6.

The plasmids of the transformants thus obtained are examined by rapid analysis on an agarose gel as described above. This shows that the recombinant expression plasmid molecules have a higher molecular weight than the expression plasmids without insertion.

One of the recombinant expression plasmids is used for subsequent experiments and is called pWH1307. It is cleaved with the restriction endonucleases Hind III and Sal I and eluted from a gel as described above. The recombinant phage DNA pWH1301 is then likewise cleaved with the restriction endonucleases Hind III and Sal I. The DNA fragment 1400 bp in size which results from this is eluted from a gel as described above.

Subsequently, the DNA fragment 1400 bp in size from pWH1301 is inserted into the large Hind III-Sal I fragment of the expression plasmid pWH1307. The ligation, transformation and identification of the desired ligation product are carried out in accordance with the construction of the recombinant expression plasmid pWH1307.

The new recombinant expression plasmid according to the invention which is obtained in this way is called pWH1372 and is used for the subsequent expression.

FIG. 8 shows a diagram of the construction of the recombinant expression plasmid pWH1372.

EXAMPLE 7

Determination of the nucleotide sequence of the mutarotase gene

The sequence of the gene was determined by the method of Makam and Gilbert. The sequencing strategy is depicted in Table VI.

The nucleotide sequence corresponds to the DNA sequence depicted in FIG. 10. The DNA sequence shows that a signal sequence is located upstream of the codon determined by N-terminal amino acid sequencing. Hence the amino acid sequence of the polypeptide which is formed starting from the recombinant expression plasmid pWH1372 and has the biological activity of the enzyme mutarotase is that depicted in FIG. 11.

EXAMPLE 8

Expression of the mutarotase gene with the expression plasmid pWH1372 in E.coli 69

The E.coli strain No. 69 (E.coli K12 ΔH1) is transformed with the new recombinant expression plasmid pWH1372 according to the invention. This strain of host bacteria contains on its chromosome a locus which codes for the thermolabile repressor CI857. Hence, in this strain, the transcription controlled by the λ-P$_L$ promotor is completely inhibited at 32° C. but is not inhibited at 40° C. because the thermolabile repressor CI857 is in its inactive form at this temperature.

In a typical expression procedure, 200 ml of LB medium (10 g/l tryptone, 8 g/l NaCl, 5 g/l yeast extract, pH 7.8) are inoculated with 3 ml of an overnight culture of E.coli 69/pWH1372, and cultivation is continued at 28° C. to a cell density of 0.68 OD. The culture is then shaken further in a shaker in a waterbath at 40° C. The mutarotase activity is detected after the subsequent cell disruption.

1 ml of the cell culture is centrifuged down, and the cells are resuspended in 100 μl of disruption buffer (50 mM Tris-HCl, pH 8.0, 1 mM EDTA, 5–8% triton). After addition of 10 μl of lysozyme (25 mg/ml in 50 mM Tris.HCl, pH 8.0, 1 mM EDTA), the cells are incubated at 28° C. for 10 minutes and at 45° C. for 5 minutes. The cells are then centrifuged down, and the supernatant is examined for mutarotase activity. The expression found with 6000 U/l of culture medium exceeds the expression of the bacterium Acinetobacter in shaken flasks by a factor of approximately 60.

TABLE VI

Sequencing strategy

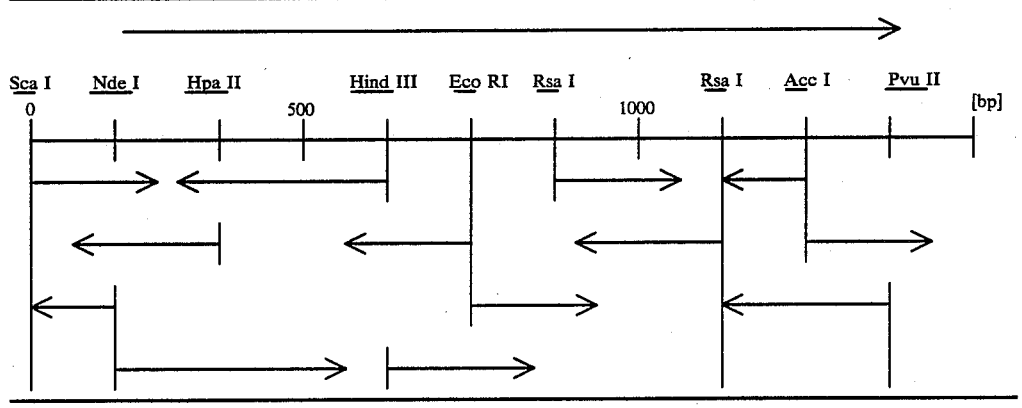

The vertical lines in the drawing show the restriction sites at which the radiolabelling was placed for the sequencing. The arrows indicate how far the sequence can be read.

The sequence between the Sca I and Hind III sites was determined in pWH1318 and pWH1372. The sequence between the two RsaI sites was determined after cloning in pUR250 (28).

The strain E.coli No. 69/pWH1372 forms about 20 mg of mutarotase per l of culture medium. On optimization of fermentation on the industrial scale, the yields of expression mutarotase may be set at a factor of 3 to 50 compared with the indicated figure.

EXAMPLE 9

Purification and analysis of the mutarotase expressed in E.coli

As is shown in FIG. 9, about 90% of the synthesized mutarotase is located in the medium.

The proteins in 1 l of medium are precipitated out with 90% ammonium sulfate, resuspended, dialysed against 20 mM $KH_2PO_4/K_2HPO_4$, pH 9.0, and adsorbed onto a CM-Sephadex column (1 cm×20 cm). Elution is carried out with the same salt conditions as described in Example 1, the mutarotase being released from the column material at mM $K_2HPO_4/KH_2PO_4$, pH 9.0. Table VII summarizes the purification scheme. The purity of mutarotase before and after the purification steps is evident from tracks MUT and P of the SDS gel (FIG. 9). The Bradford method was used for determining the protein here.

TABLE VII

|  | Activity (U) | Spec. activity (U/mg) | Protein (mg) | Yield (%) |
|---|---|---|---|---|
| Medium | 4700 | ND | ND | 100 |
| Ammonium sulfate precipitation | 4690 | 69 | 68 | 99 |
| Dialysis | 2800 | 54 | 52 | 60 |
| CM-Sephadex | 2400 | 200 | 12 | 52 |

12 mg of protein are isolated from 1 l of medium by one precipitation and one purification step by column chromatography. The specific activity is about 14% lower than that of mutarotase isolated from A.calcoaceticus. The product isolated from *E.coli* has a molecular weight, determined on a denaturing polyacrylamide gel, of 40 kDa. This molecular weight agrees with that of the protein isolated from A.calcoaceticus.

Sequencing of the N-terminal amino acids of the mutarotase isolated from the *E.coli* medium showed that the preparation had provided a homogeneous product whose N-terminal sequence was as follows:

Ala Thr Leu Asn Val Lys Ser Tyr Gly

The N-terminal amino acids of the two products agree. However, there is a serine at position 7 whereas the mutarotase from A.calcoaceticus has a proline at this position.

The following properties are similar for the mutarotase expressed in *E.coli* and the mutarotase expressed in A.calcoaceticus:

1. There is a difference of only around 14% in the specific activity.
2. The two proteins have the same molecular weight on a denaturing polyacrylamide gel.
3. Both proteins bind to CM-Sephadex ion exchanger material at 20 mM $K_2HPO_4/KH_2PO_4$, pH 9.0.
4. The two proteins have the same amino acid composition.
5. The two proteins have the same N-terminal sequence.
6. Both proteins pass through the inner membrane. However, mutarotase is released into the medium only in *E.coli*.

This demonstrates that the desired product can be expressed in *E.coli*. Under comparable conditions, the *E.coli* strain produces 50–100 times more mutarotase than the A.calcoaceticus originally used. The product can be prepared from *E.coli* with fewer purification steps.

Mutants:

The DNA-molecules, polypeptides, expression plasmids, and host organisms as described above embrace as well mutants or variants thereof caused e.g. by radiation, temperature effects, chemical or biological influences, whenever they exhibit the biological activity of mutarotase.

REFERENCES

1. Zabeau, M. and Roberts, R. (1979) in: "Molecular Genetics" (J. H. Taylor, ed.), Academic Press, New York, Part III, pp. 1–63
2. Ehrlich, M., Cohen, S., and McDeuitto, (1978) Cell 13, 681–689
3. Broome, S. and Gilbert, W. (1978) Proc. Natl. Acad. Sci. USA 75, 2746–2749
4. Clark, L., Hitzeman, R., and Carbon, J. (1979) Methods in Enzymol. 68, 436–442
5. Laemmlie, U.K. (1970) Nature 227, 680–685
6. Bradford, M.M. (1976) Anal. Biochem. 72, 248–254
7. Edman, P. and Henschen, A. (1975) in: "Molecular Biology, Biochemistry Biophysics" (S. B. Needleman, ed.), Vol. 8, pp. 232–279, Springer Verlag, Berlin
8. Zimmermann, C. L., Appella, E., and Pisano, J. J. (1980), Anal. Biochem. 77, 569–573
9. Salnikow, J., Lehmann, A., and Wittmann-Liebold, B. (1981), Anal. Biochem. 117, 433–442
10. Laurson, R. A. (1970) Eur. J. Biochem. 26, 89–102
11. Steffens, G.J. and Buse, G. (1976) Hoppe Seyler's Z. Physiolog. Chemie 357, 1125–1137
12. Gross, E., Wittkopp, B. (1961) J. Am. Chem. Soc. 83, 1510–1514
13. Titani, K., Sagasawi, T., Resing, K., and Walsh, K. A. (1982), Anal. Biochem. 123, 408–412
14. Mattevcci, M. D. and Caruthers, M. H. (1981) J. Am. Chem. Soc. 103, 3185–3191
15. Beaucage, S. L. and Caruthers, M. H. (1981) Tetrahedron Lett. 22, 1859–1862
16. Greene, D. J. et al. (1978) Nucl. Acids Res. 5, 2373–2390
17. Helling, R. B., Goodman, H. M., and Boyer, H. W. (1974), J. Virol. 14, 1235–1244
18. Blakesley, R. W. and Wells, R. D. (1975) Nature 257, 421–422
19. Hardies, S. C., Patient, R. K., Klein, R. D., Ho, E., Reznikoff, W. S., and Wells, R. D. (1979), J. Biol. Chem 254, 5527–5534
20. Messing, J. (1983) Meth. Enzymol. 101, 20–78
21. Maxam, A. and Gilbert, W. (1980) Meth. Enzymol. 65, 499–580
22. Wallace, R. B., Schold, M., Johanson, M. J., Dembed, P., and Itakura, K. (1981), Nucleic Acids Res. 9, 3637–3656
23. Walseth T. F. and Johnson, R. A. (1979) Biochim. Biophys. Acta 526, 11–31
24. Weinstock, R., Sweet, R., Weiss, M., Cedar, H., and Axel, R. (1978), Proc. Natl. Acad. Sci. U.S.A. 75, 1299–1301
25. Southern, E. M. (1975) J.Mol. Biol. 98, 503–517
26. Wahl, G. M., Stern, M., and Stark, G. R. (1979) Proc. Natl. Acad. Sci. USA 76, 3683–3687
27. Messing, J., Crea, R., and Seeburg, H. (1981) Nucleic Acids Res. 9, 309–321
28. Rüther, U. (1982) Nucleic Acids Res. 10, 5765–5772
29. Soberon, C., Coverrubais, L., and Bolivar, F. (1980) Gene 9, 287–305

30. Bolivar, F., Rodriquez, R. L., Greene, P. J., Betlach, M. C., Heynecker, H. L., and Boyer, N. W. (1977), Gene 2, 95-113

31. Stucliffe, J. G. (1978) Nucleic Acids Res. 5, 2721-2728

32. Remaut, E., Staussens, P., and Fiers, W. (1981) Gene 15, 81-93

33. Bernard, H. U. and Helinski, D. R. (1979) Meth. Enzymol. 68, 482-492

34. Winnacker, E. L. (1985), Gene und Klone, VCH-Verlag

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An isolated DNA molecular consisting essentially of a DNA sequence derived from the genome of a microorganism of the genus Acinetobacter and coding for a polypeptide having the biological activity of the enzyme mutarotase, wherein, when said DNA molecular is expressed in *E. coli*, the resultant protein is secreted into the medium in which said *E. coli* is grown in amounts substantially greater than when said DNA molecular is expressed in the Acinetobacter from which it is derived.

2. An isolated DNA molecular consisting essentially of a DNA sequence derived from the genome of a microorganism of the genus Acinetobacter and coding for a polypeptide having the biological activity of the enzyme mutarotase, or consisting essentially of a different DNA sequence which hybridizes with said Acinetobacter sequence and which codes for a polypeptide having the biological activity of the enzyme mutarotase, wherein, when said DNA molecule is expressed in *E. coli*, the resultant protein is secreted into the medium in which said *E. coli* is grown in amounts substantially greater than when said DNA molecule is expressed in the Acinetobacter from which it is derived.

3. A DNA molecule of claim 2, wherein the microorganism is Acinetobacter calcoaceticus DSM 30007, DSM 30008, DSM 30010 or DSM 30011.

4. A recombinant cloning vector comprising a DNA sequence of claim 2.

5. A recombinant cloning vector of claim 4, wherein said sequence is functionally connected to an expression control sequence.

6. A recombinant cloning vector of claim 5, wherein the control sequence is an *E. coli* promoter system.

7. A method for producing a polypeptide having the biological activity of the enzyme mutarotase comprising expressing the corresponding DNA sequence of a vector of claim 5.

8. An isolated sequence

```
ATGAAAAAATTAGCAATTTTAGGTGTTACGGTTTATAGCTTTGCACAACT
GGCAAATGCAGCAACGTTAAATGTAAAATCATATGGTACGACTCAAAATG
GCCAAAAAGTTGATCTATACACCATGAGTAATAACAATGGAGTCTCGGTA
TCTTTTATTAGTTTTGGTGGTGTAATTACACAAATCTTGACTCCCGATGC
CCAAGGCAAACAAAATAATATCGTTTTGGGCTTTGATGACTTAAAAGGCT
ATGAAGTCACTGATACCAAGGAAGGTATTCATTTTGGCGGATTAATTGGT
CGTTATGCGAACCGGATTGGCAATGCTAAATTTAGCTTAGATGGAAAAAC
GTATAACCTCGAAAAAAATAATGGTCCGAACTCATTACATAGCGGCAATC
CTGGTTTTGATAAACGTGTTTGGCAAGTTAAGCCCCTCGTTTCTAAAGGT
GAAACCGTTAAAGCTTCTCTTAAGTTAACCAGCCCAAATGGAGATCAAGG
TTTTCCCGGAAAATTAGATGTAGAAGTGATCTACAGTCTTTCAGATCAAA
ATGAATTCAAGATTGAATATAAAGCCAAAACTGATCAGCCTACAGTCGTC
AACCTTACCAACCACAGTTATTTCAACTTATCAGGTGCTGGGAACAATCC
TTATGGCGTGCTAGATCATGTGGTACAACTCAATGCAGGCCGTATTCTGG
TAACCGATCAAAACTCTTTACCAACAGGTGAAATTGCTTCAGTTGCAGGT
ACGCCTTTTGATTTTCGGATGCCTAAAGCAATCGTAAAAGATATTCGAGC
AAATAATCAGCAATTGGCCTATGGATATGGCTATGACCAAACTTGGGTAA
TTAATCAAAAGTCTCAAGGAAAACTCAATCTTGCAGCTATTGTGGTTGAT
CCAAAATCTAAACGGACCATGCAAGTCTTAACCACTGAACCAAGCGTCCA
AATGTATACAGCCGATCATTTATTAGGAAATATTGTTGGCGCAAATGGCG
TACTCTATCGACAAGCAGACGCACTAGCATTAGAAACACAGCATTTTCCA
GACAGCCCGAATCAACCAACTTTCCCGTCTACACGTTTAAACCCAAATCA
AACTTATAACAGTGTTACCGTATTTAAGTTTGGTGTTCAAAAA
``` coding for a polypeptide having the biological activity of the enzyme mutarose.

9. A recombinant cloning vector comprising a DNA sequence of claim 8.

10. A recombinant cloning vector of claim 9, wherein said sequence is functionally connected to an expression control sequence.

11. A recombinant cloning vector of claim 10, wherein the control sequence is an *E. coli* promoter system.

12. A microorganism or cell culture transformed with a vector of claim 11.

13. A method for producing a polypeptide having the biological activity of the enzyme mutarose comprising expressing the corresponding DNA sequence of a vector of claim 9.

14. A method for producing a polypeptide having the biological activity of the enzyme mutarotase comprising expressing the corresponding DNA sequence of a vector of claim 11.

15. Plasmid pWH1372 (DSM 3443P).

16. A method for producing a polypeptide having the biological activity of the enzyme mutarotase comprising expressing the corresponding DNA sequence of plasmid of claim 15.

17. *E. coli* WH 1372 (DSM 3442).

* * * * *

UNITED STATES PATENT AND TRADEMARK OFFICE
CERTIFICATE OF CORRECTION

PATENT NO. : 4,963,488
DATED : October 16, 1990
INVENTOR(S) : Gatz et al It is certified that error appears in the above-identified patent and that said Letters Patent is hereby corrected as shown below:

Column 24, Claim 8, Line 40:

Should read: --of the enzyme mutarotase.--

Column 24, Claim 13, Line 52:

Should Read: --biological activity of the enzyme mutarotase comprising--

Signed and Sealed this

Twenty-first Day of April, 1992

*Attest:*

HARRY F. MANBECK, JR.

*Attesting Officer*      *Commissioner of Patents and Trademarks*